United States Patent [19]

Tamers

[11] 4,009,219
[45] Feb. 22, 1977

[54] TOTAL SYNTHESIS OF BENZENE FROM NON-HYDROCARBON MATERIALS

[76] Inventor: Murry A. Tamers, Nova University College Ave., Fort Lauderdale, Fla. 33314

[22] Filed: Apr. 28, 1975

[21] Appl. No.: 572,165

[52] U.S. Cl. .......................... 260/673; 260/679 R; 423/439
[51] Int. Cl.$^2$ .................... C07C 3/02; C07C 11/24
[58] Field of Search ............. 260/673, 679, 666 XA

[56] References Cited

UNITED STATES PATENTS

| | | | |
|---|---|---|---|
| 2,642,347 | 6/1953 | Gilbert | 48/216 |
| 2,802,723 | 8/1957 | Lemke | 423/439 |
| 2,846,940 | 8/1958 | Witt | 260/673 |
| 3,365,510 | 1/1968 | Noakes | 260/673 |
| 3,655,804 | 4/1972 | Pennella | 260/678 |
| 3,714,323 | 1/1973 | Dolci et al. | 423/4 |

OTHER PUBLICATIONS

M. A. Tamers "Synthesis of Liquid Scintillation Solvents" Molecuar Crystals 4 261–276 (1968).
Acta Cientifica Venezolana 16, No. 5, 156–162 (1965).

*Primary Examiner*—Delbert E. Gantz
*Assistant Examiner*—G. E. Schmitkons
*Attorney, Agent, or Firm*—Oltman and Flynn

[57] ABSTRACT

A method of producing benzene on a high yield basis is disclosed in which non-hdyrocarbon carbonaceous raw materials are reacted with an alkali metal or an alkaline earth metal in the form of molten metal, metallic hydroxide or metallic oxide to produce the metallic carbide; the metallic carbide is hydrolyzed to produce acetylene; and the acetylene is cyclized to benzene. Side reactions are controlled to maximize yields. Benzene may be used to extend gasoline.

10 Claims, No Drawings

TOTAL SYNTHESIS OF BENZENE FROM NON-HYDROCARBON MATERIALS

BACKGROUND OF THE INVENTION

Early work on production of benzene is described in "Molecular Crystals", 1968, Vol. 4, pp 261–276; and "Acta Cientifica Venezolana", Vol. 16, No. 5, pp 156–162 (1965). The present invention involves the improvement of yields and efficiencies in the basis reactions by controlling side reactions.

SUMMARY OF THE INVENTION

This invention relates to systems for the production of benzene from non-hydrocarbon raw materials. It involves the discovery of yield-reducing secondary reactions in various steps of the total syntheses and techniques for their minimization. The intermediates in the syntheses are recyclable and methods are described for this. The invention is applicable to a large variety of raw materials: coal, coke; and other fossil fuel chars; agricultural materials; forestry products of all types, including leaves, twigs, bark, wood chips, wood and charcoal; household wastes; animal wastes; carbonates, including all limestones and dolomites, caliche, shells, water carbonate species; carbon dioxide; and carbon monoxide.

The procedures consist of four general steps: 1. The production of carbides from the raw materials by direct reaction with molten metal, metallic hydroxide, or metallic oxide; the metal being alkali or alkaline earth metal; 2. The hydrolysis of the carbide to produce acetylene gas; 3. The regeneration of the reactant metal, hydroxide, or oxide; and 4. The conversion of the acetylene gas to benzene.

DESCRIPTION

I prepare carbides by the following reactions:

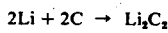  (A)

  (B)

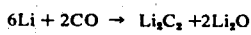  (C)

  (D)

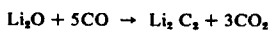  (E)

  (F)

  (G)

The reactions are all carried out in the strict exclusion of air. Lithium is ordinarily preferred as the alkali metal, but sodium, potassium, and cesium are likewise useful. However, the temperatures recommended are specially for the lithium case. Alkaline earth metals are also applicable. It will be realized that any of the alkali metals or alkali earth metals can be substituted for lithium in the reactions (B), (C), (E), and (F). However, in reactions (A) and (G), if the carbon source is coke or any other high ash content material, alkali metals would preferably be used because of the solubility of their hydroxides, which facilitates the separation of the coke ashes. In reaction (D), only calcium or an alkali metal would be practical due to the necessity of reclaiming the products after the carbide hydrolysis.

Reaction (A) describes the production of a carbide employing coke, chars, charcoal, or other carbonized organic material. In order for the reaction to use the metal with the highest efficiency, it is necessary to take precautions to minimize the occurrence of various metal consuming side reactions. These do not disrupt the primary reaction, but the unnecessary consumption of the metal requires additional energy to be used in its recycling, thus elevating the total cost of the acetylene production. It is preferable that the chars contain as high a content of carbon as possible. This can be achieved by choosing low ask materials and destructively heating the raw material, in the absence of air, to a high temperature, preferably 1000° C, to insure its complete carbonization. As much hydrogen, oxygen, and nitrogen as possible should be dirven off, since these elements in all their forms will consume the metal during the carbide preparation.

For the materials of reaction (A), it has been found that the optimum procedure is to begin the operation by a preliminary heating of the raw material to 1000° C in vacuum. The evolved gases are collected and the water discarded. The principal gas is hydrogen, which is retained for other industrial processes. After heating at 1000° C for a time sufficient to complete the degasing, usually at least 30 minutes, a slightly less than stoichiometric amount of lithium metal, for example, is allowed to come in contact with the carbonaceous material. Reaction (A) proceeds exothermically and spontaneously. The mix is allowed to sit at about 1000° C for at least 30 minutes. Higher temperatures are not employed in order to avoid the excessive voltilization of the metal. In order to handle this problem at the recommended temperature, the reactor vessel is heated only at the locality of the reactant mix and is sufficiently long to permit the condensation of the liquid metal on the sides above the intensely heated zone, thus permitting the subsequent gravity return of the condensed metallic vapor to the reaction zone. Less than 1000° C is not recommended since this causes slow reactions and low yields of the carbide.

The less than stoichiometric amount of metal insures the complete usage of this material. The cost of recycling the metal reactant or the carbide is greater than the value of the raw material. If the raw material has excessive amounts of other metal oxides, more metal reactant should be employed since there will be losses due to the reduction of the oxides with the molten alkali metal. During the hydrolysis of the carbide (reaction (M) described in a following paragraph) the unreacted metals will produce hydrogen gas. This is separated from the acetylene and collected for other industrial uses. The exploitation of the hydrogen gas partially compensates for the alkali metal consumed, but it is economically advantageous to minimize these secondary reactions.

In reaction (B), molten alkali or alkali earth metal is reacted with carbon dioxide gas. This is done by first bringing the metal to 700° C in vacuum. At this point, the carban dioxide gas is allowed to slowly enter the reaction chamber. Reaction (B) is exothermic and spontaneous. The gas feeding is regulated to maintain the temperature, but to also avoid the sputtering of the reaction mixture. This results in the deposition of lithium metal in cold portions of the reactor, thus removing the metal from the reaction zone.

At 700° C reaction (B) proceeds rapidly. At a higher temperature, there occurs the excessive production of carbon and carbonate by the secondary reaction (H), to be described in a following paragraph. At less than 700° C the entering carbon dioxide is preferentially absorbed by secondary reaction (I), discussed later, instead of the carbide producing primary reaction (B).

When the carbon dioxide has finished its reaction at 700° C, the temperature is brought up to 1000° C and kept there for at least 30 minutes. This is to reverse secondary reactions and permit the reaction of the evolved carbon dioxide to produce carbide through further attempts at primary reation (B). The carbon produced in a secondary reaction would react with the remaining molten metal through (A). During this time and in all other reations, the reactor is operated under vacuum, but without the vacuum pumping system connected. It is essential for the reactor to be made as leak proof as possible.

Reaction (B) presents an advantage over (A) in that there are no ashes introduced into the reactor vessel. This permits, after drying, the direct recycling of the alkali metal oxide in the reactor itself, thus eliminating the possibility of losses during a filtering operation necessary to separate the reactant metal oxide from the ashes. It also eliminates the necessity of the use of an excess of water to solubilize the oxide and the following salting out operation, to be described later. However, reaction (B) has the disadvantage of requiring 5 times the amount of lithium as reaction (A). But the raw material of (B) should be considerably less costly than that of (A) and in special situations would be cost-free.

The production of carbide by reaction (C) provides the advantage of ashes-free operation, but requires only three-fifths of the metal of reaction (B). The temperature conditions for optimum performance here are identical to that described for (B). The carbon monoxide gas is produced by the partial oxidation of any carbonaceous material with standard methods. If the industrial operation for carbon monoxide gas generation is available, it would be most advantageous to produce the carbide by combination of reactions (C) and (E). Carbon is produced in significant quantities through a reaction similar to (H) and by the thermal decomposition of carbon monoxide at 700° C to carbon and carbon dioxide. The carbon dioxide would be used by reaction (B). In and industrial process consisting of a combination of reactions (C) and (E), the recycling and carbide production steps would be done simultaneously.

Reaction (D) proceeds spontaneously when a charge of lithium metal, for example, and carbonate are heated in vacuum to 500° C. The optimum reaction conditions are to bring the temperature to at least 700° C as rapidly as possible and to allow the temperature to rise to 1000° C to reverse the secondary reactions that have produced carbon and reactant metal oxide. The temperature is maintained at 1000° C for 30 minutes. If higher temperatures are used, the reduction of the calcium oxide by alkali metal will be excessive.

After the acetylene producing hydrolysis, the calcium oxide is filtered out and exploited in other industrial processes. Reaction (D) would be advantageous in situations where it is desirable to produce quantities of calcium oxide from carbonates raw material. This operation would be combined with the acetylene production.

Reaction (G) must be carried out under vacuum conditions of at least 0.1 torr and at least 1000° C. In contrast to the other reactions discussed previously, it is essential to have the vacuum pumping system continuously connected to the reactor and to remove the gas produced during the reaction. The entire operation consists of charging the reactor with stoichiometric amounts of alkali metal oxide and reduced carbonaceous raw material. The drying of the oxide can be carried out here during the initial stages of heating. Both carbide and reactant metal are produced during the process. The reactor is heated on the bottom, where the charge lies. In the case of lithium, for example, vapor condenses on the upper portions of the chamber and flows back down into the reaction area. It forms the carbide through reaction (A). The entire process increases in rate with temperature and degree of vacuum. This procedure combines the intermediates recycling and alkali metal carbide operations.

For reactions (E) and (F) the best conditions are approximately 500° C and high pressures of carbon monoxide gas. Of the order of 100 atmospheres are necessary to drive the reactions toward the carbide product. Higher temperatures are not feasible due to the decomposition of carbon monoxide to carbon and carbon dioxide. This gas is absorbed by the alkali metal oxide, thus removing the latter from reaction with carbon monoxide. These reactions are best carried out in cycles. Initially, there is a period of reaction with carbon monoxide at high pressures and 500° C. The carbon monoxide and acetylene (generated from the reaction of the water and carbide products in the case of reaction (F)) are then removed and the alkali metal carbonates decomposed at higher temperature. The evolved carbon dioxide is discarded. The reaction mixture is brought back to 500° C and the carbon monoxide re-introduced at high pressure. This cycle is repeated several times to permit the efficient use of the reactant metal oxide. After a final hydrolysis, especially for reation (E), the carbon by-product is filtered out and the lithium oxide re-submitted to reaction. The carbon is combusted to form additional carbon monoxide.

The employment of reactions (E), (F) and (G) for lithium carbide production have the advantages of not requiring working with reactant in the metallic state and combining recycling and production steps. Reactions (E) and (f) operate at relatively low temperatures, but are the only reactions described here that require high pressures.

In the reactions involving reactant metals, various side reactions can occur that consume the reactant. The major possibilities are, using lithium as an example:

$$4Li + 2CO_2 \rightarrow Li_2CO_3 + C + Li_2O \quad (H)$$

$$Li_2O + CO_2 \rightarrow Li_2CO_3 \quad (I)$$

$$6Li + N_2 \rightarrow 2Li_3N \quad (J)$$

$$4Li + O_2 \rightarrow 2Li_2O \quad (K)$$

$$4Li + H_2O \rightarrow Li_2O + 2LiH \quad (L)$$

$$Li(Solid) \rightarrow Li(Liguid) \rightarrow Li(gas) \quad (M)$$

Reactions (H) and (I) are prevalent in the operations of reactions of metals with carbon dioxide and carbonates. They are minimized by the temperature schedules described previously. Reactions (J), (K), and (L) are due to leaks in the reactor, permitting the entrance of air, or humidity left in the system from a proceeding hydrolysis. It is very important to avoid these consumptions of the metal reactant; they seriously disfavor the economics of the method of carbide production. It should be noted that four to six moles of lithium are used up for every mole of these contaminants that enter.

Side reaction (M) involves the volatilization of the lithium metal reactant. It is important that the reactor be constructed so that the lithium vapor condensation takes place on portions of the reactor that are at least 300° to 700° C. In this case the metal remains liquid and can flow back to the reaction zone.

The lithium metal carbide has an important advantage in that the heat of the acetylene producing hydrolysis reaction is considerably less than that of the common calcium carbide acetylene generation. With lithium carbide, it is feasible to add water directly to the carbide, thus:

$$Li_2C_2 + H_2O \rightarrow C_2H_2 + Li_2O \quad (N)$$

It is not necessary to provide a separate system in which the carbide is removed from the reactor and transferred to another locality where it is broken into small pieces and added to water, as is done in the calcium carbide systems.

Following the acetylene production, the lithium oxide is recuperated by the following steps in the case of reaction (A):
1. Sufficient water is added in the carbide hydrolysis to guarantee the complete solubility of lithium hydroxide. The raw material ashes are centrifuged out.
2. The ask cake is washed with water to recover traces of lithium salts. This water is used for the next carbide hydrolysis.
3. To the supernatent liquid of 1. is added a concentrated sodium hydroxide solution. Lithium hydroxide is salted out and removed by centrifugation.
4. The supernatent liquid of 3. is concentrated by evaporation and used in the next batch for step 3.
5. The lithium hydroxide is thermally decomposed to lithium oxide if it is to be used in reactions (E) or (G) to regenerate lithium carbide, or
6. The lithium hydroxide is converted to lithium chloride by the addition of hydrochloric acid. It is dehydrated and then, with potassium chloride mixed in, decomposed by a fused salt electrolysis. The lithium metal produced is used in reactions (A), (B), (C) or (D) to produce further lithium carbide.

The acetylene to benzene cyclization is exothermic and spontaneous.

$$3 C_2H_2 \rightarrow C_6H_6 \quad (O)$$

The reaction can be accelerated by a large variety of catalysts. A chromium VI or vanadium VI activated silica-alumina catalyst is preferred and the side reactions that reduce benzene yields and cause deactivation of the catalyst have been elucidated.

As an example, 2mm silica-alumina pellets activated by 0.2 % (by weight) potassium chromate has been investigated (see U.S. Pat. No. 3,365,510, by J. Noakes). Under the optimum conditions I have elucidated, the yields of the acetylene to benzene reaction are up to 99+%. Much of the catalyst deactivation and acetylene loss has been determined as due to the following important secondary reactions:

$$3C_2H_2 + 10K_2CrO_4 \rightarrow 6K_2CO_3 + 5Cr_2O_3 + 3H_2O + 4K_2O \quad (P)$$

$$C_2H_2 + 5K_2CrO_4 \rightarrow 2K_2CO_3 + 5CrO_2 + H_2O + 3K_2O \quad (Q)$$

Mechanisms involving intermediates, particularly acetaldehyde and acetic acid have been seen to occur. This is in agreement with the discovery that small amounts of moisture in the acetylene or on the catfalyst cause rapid catalyst deactivation in addition to lower benzene yields. The reactions are the following:

$$C_2H_2 + H_2O \rightarrow CH_3CHO \quad (R)$$

$$3CH_3CHO + 2K_2CrO_4 \rightarrow 3CH_3COOK + Cr_2O_3 + KOH \quad (S)$$

$$3CH_3COOK + 8K_2CrO_4 \rightarrow 6K_2CO_3 + 4Cr_2O_3 + KOH + 3K_2O + H_2O \quad (T)$$

Acetaldehyde being very reactive, (S) proceeds readily at all temperatures. Acetate is more stable and, therefore, (T) is most significant at excessive catalyst heatings. Polymers can also be formed by the reaction of acetaldehyde or acetate with acetylene.

Reduction of the chromate by hydrogen gas, formed in small amounts by the decomposition of acetylene, also occurs. This is avoided by keeping the catalyst temperature below 200° C. Low temperatures are maintained by regulating the flow of acetylene onto the catalyst and cooling the latter.

Thorough drying of the catalyst and the acetylene is very important to insure good yields and a low rate of catalyst deactivation. The catalyst should be desiccated at above 300° C under good vacuum for at least an hour. Precautions must be taken to prevent the absorption of water vapor drawn out of the pump itself. The acetylene can be dried with ordinary methods after being purified of the principal impurities, ammonia, hydrogen sulfide, phosphine, and hydrogen, all of which cause catalyst deactivation. The pure dry acetylene is put on the catalyst at room temperature. Benzene is extracted by heating the catalyst to about 120° C.

The catalyst can be readily reactivated by heating in air at about 500° C, which causes the oxidation of the $Cr^{III}$ and $Cr^{IV}$ to $Cr^{VI}$. Any carbon produced by acetylene decomposition is burned off at the temperature. Higher temperatures should not be employed, since the chromium would begin to react with the silica-alumina base and the catalyst capacity permanently reduced. The situation is similar in the case of vanadium activated silica-alumina catalysts. The deactivation here involves an oxidation state reduction, form $V^V$ to $V^{IV}$ and $V^{III}$. Reactivation of this catalyst proceeds readily in air at 500° C.

The following examples are illustrative of the invention.

EXAMPLE 1

A 26.0 grams sample of Miami Oolite limestone and 8.7 grams of lithium metal were heated together in an evacuated stainless steel tube. A noticeable reaction began at 600° C, as evidenced by an evolution of gas, which was quickly readsorbed. The temperature was finally brought up to 1000° C and held there for 30 minutes. After cooling the system to room temperature, water was added to produce acetylene gas. The dried and purified acetylene occupied a volume of 5.08 liters at standard temperature and pressure. Less than 0.1 liter STP hydrogen gas was produced. The dried acetylene on a dried potassium chromate activated silica-alumina catalyst produced 5.9 gm benzene.

EXAMPLE 2

A caron dioxide sample was obtained through the decomposition of limestone by perchloric acid. After thorough drying, the gas occupied 9.88 liters at standard temperature and pressure. 15.3 grams of lithium metal was placed in a stainless steel chamber that was quickly evacuated. A dry ice cooled trap prevented the introduction of water or other vapors into the system from the vacuum pump oil. The lithium was heated to 700° C and the carbon dioxide gas introduced. The gas reacted in less than 5 minutes. The temperature was then increased to 1000° C and held there for 30 minutes. After cooling to room temperature, water was introduced. Tehe evolved acetylene was dried and separated from small amounts of hydrogen. The acetylene produced occupied a volume of 4.80 liters, corrected to standard temperature and pressure. 5.5 gm benzene were obtained from a reaction on a potassium chromate activated silica-alumina catalyst.

EXAMPLE 3

A sample of 12.5 grams wood charcoal, very clean, dried and thoroughly carbonized, was mixed with 7.1 gm of lithium metal. The stainless steel reaction vessel was thoroughly evacuated by a protected pump. The mixture was brought to 1000° C and held at that temperature for 30 minutes. The system was without noticeable leaks. No gas was evolved. After cooling and addition of water, the evolved acetylene was dried and collected. No hydrogen gas was observed. The acetylene occupied 11.1 liters, corrected to standard temperature and pressure. 12.9 grams of benzene were generated using a potassium chromate activated silica-alumina catalyst.

EXAMPLE 4

A sample of 24.0 grams of char from a pyrolysis type coal liquification plant (COED Process, FMC Corporation, Princeton, N.J., W. Kentucky char CRD 12087) was outgassed under vacuum at 1000° C for 30 minutes. After cooling 11.7 lithium metal was added and the reactor re-evacuated. The lithium used in this case was of the poorest quality and had considerable amounts of oxides and nitrides throughout. A reaction was carried out at 1000° C. After cooling and hydrolysis, the acetylene produced was dried and converted to benzene on a potassium chromate activated silica-alumina catalyst. 15.0 grams benzene were obtained. This would be equivalent to 13 liters of acetylene, corrected to standard temperature and pressure.

EXAMPLE 5

A sample of 5.09 liters of carbon monoxide was generated by the attack of formic acid by concentrated sulfur acid. The gas was dried by passage over dry ice cooled traps. The carbon monoxide was let into an evacuated reactor containing 5.0 grams of lithium metal at 700° C. The gas was totally absorbed in 15 minutes. The temperature was then brought to 1000° C and held there for 30 minutes. Some gas came off at this time, but was reabsorbed. After cooling and hydrolysis, acetylene was collected in a liquid nitrogen cooled trap and some hydrogen pumped off. Expansion of the acetylene into a vessel of known volume permitted its measurement. A total of 2.32 liters of the gas, corrected to standard temperature and pressure, was obtained. From this, 2.6 grams benzene was formed using a potassium chromate activated silica-alumina catalyst.

EXAMPLE 6

A sample of 2 grams lithium carbonate and 3 grams char (containing 60% carbon) were heated under vacuum in an induction furnace. Initially, water, hydrogen and carbon dioxide evolved and were removed. Later, the mixed powder was brought to 1000° C and a vacuum of 0.1 torr attained. A reaction started at this point that produced lithium metal vapor. Only at this temperature and vacuum could the reaction commence. After cooling, it was observed that both lithium and lithium carbide were present. These compounds were subsequently hydrolyzed to produce hydrogen and acetylene.

EXAMPLE 7

The effect of insufficient drying of the acetylene gas on the benzene yield was investigated and the results are shown in Table 1. Potassium chromate catalysts that had been thoroughly dried were used in these experiments. Catalyst temperatures were kept below 160° C in all cases by external cooling and regulation of the gas flow.

EXAMPLE 8

The effect of excessive catalyst temperature on acetylene to benzene yields was investigated and the results are shown in Table 2. Potassium chromate catalysts were used. Both the catalysts and acetylene samples had been thoroughly dried beforehand.

TABLE 1

Acetylene to benzene yield as a function of humidity of the reactant.

| Acetylene used | Moisture added | Benzene obtained | Yield |
|---|---|---|---|
| 4.91 liters (STP) | 5.0% | 4.9 gm | 86% |
| 3.65 | 3.5% | 4.0 | 94 |
| 4.90 | 2.6% | 5.5 | 96 |

TABLE 2

Acetylene to benzene yield as a function of maximum temperature of catalyst.

| Acetylene | Maximum temperature of catalyst | Benzene obtained | Yield |
|---|---|---|---|
| 5.10 liters (STP) | 20° C | 5.8 gm | 98% |
| 4.94 | 100° | 5.7 | 99 |
| 5.10 | 200° | 5.9 | 99 |
| 4.94 | 215° | 5.4 | 94 |
| 4.94 | 235° | 4.6 | 80 |

Having thus described my invention, I claim:
1. The process of producing benzene comprising:
a. reacting non-hydrocarbon carbonaceous material in a sealed, substantially leak-free reactor with lithium in the form of lithium metal, lithium hydroxide or lithium oxide at a temperature of at least 500° C in the strict absence of air and moisture to produce lithium carbide;

b. hydrolyzing said lithium carbide to produce acetylene and lithium in at least one of said forms;

c. cyclizing said acetylene to produce benzene;

d. and recycling through step (a) said lithium produced in step (b).

2. The process as claimed in claim 1 in which step (c) is carried out in the presence of a silica-alumina catalyst activated with a material selected from the group consisting of chromium and vanadium and in the srrict absence of moisture in both the catalyst and the reacting acetylene, and maintaining the catalyst-acetylene system below 200° C.

3. The process as claimed in claim 2 in which step (a) is carried out in high vacuum conditions produced preliminarily in said reactor by vacuum pumping and thereafter disconnecting the vacuum pump before starting said reaction.

4. The process as claimed in claim 3 in which step (a) is carried out by reacting molten lithium metal with said carbonaceous material at a temperature of about 1000° C after preliminarily degasing said carbonaceous material at a temperature of about 1000° C in the strict absence of air.

5. The process as claimed in claim 1 in which said lithium in the form of lithium metal is reacted with carbon dioxide gas first at about 700° C and then at about 1000° C during step (a).

6. The process as claimed in claim 1 in which said lithium in the form of lithium metal is reacted with carbon monoxide first at about 700° C and then at about 1000° C during step (a).

7. The process as claimed in claim 1 in which said lithium in the form of lithium metal is reacted with a metallic carbonate first at a temperature of about 700° C and then at a temperature of about 1000° C during step (a).

8. The process as claimed in claim 1 in which said lithium in the form of lithium oxide is reacted with carbon monoxide at about 500° C during step (a).

9. The process as claimed in claim 1 in which said lithium in the form of lithium hydroxide is reacted with carbon monoxide at about 500° C during step (a).

10. The process as claimed in claim 1 in which said lithium in the form of lithium oxide is reacted with carbon at a temperature of about 1000° C with high vacuum conditions and continuous efficient extraction of carbon monoxide during step (a).

* * * * *